United States Patent
Yun et al.

(10) Patent No.: US 10,613,356 B2
(45) Date of Patent: Apr. 7, 2020

(54) REMOTELY CONTROLLABLE LENS DEVICE

(71) Applicants: THE GENERAL HOSPITAL CORPORATION, Boston, MA (US); POHANG UNIVERSITY OF SCIENCE AND TECHNOLOGY, Pohang (KR)

(72) Inventors: Seok-Hyun Yun, Belmont, MA (US); Ehsan Kamrani, Montreal (CA); Sei Kwang Hahn, Kyungbuk (KR); Hyemin Kim, Daegu (KR); Dohee Keum, Busan (KR); Keon Jae Lee, Daejeon (KR); Choun-Ki Joo, Seoul (KR)

(73) Assignees: The General Hospital Corporation, Boston, MA (US); Phi Biomed Co., Ltd., Seoul (KR)

( * ) Notice: Subject to any disclaimer, the term of this patent is extended or adjusted under 35 U.S.C. 154(b) by 479 days.

(21) Appl. No.: 14/917,324

(22) PCT Filed: Sep. 9, 2014

(86) PCT No.: PCT/US2014/054698
§ 371 (c)(1),
(2) Date: Mar. 8, 2016

(87) PCT Pub. No.: WO2015/035357
PCT Pub. Date: Mar. 12, 2015

(65) Prior Publication Data
US 2016/0223842 A1    Aug. 4, 2016

Related U.S. Application Data

(60) Provisional application No. 61/875,378, filed on Sep. 9, 2013.

(51) Int. Cl.
*A61F 9/00* (2006.01)
*G02C 11/00* (2006.01)
(Continued)

(52) U.S. Cl.
CPC ............... *G02C 11/10* (2013.01); *A61F 2/16* (2013.01); *A61F 2/1624* (2013.01); *A61F 9/0017* (2013.01); *G02C 7/04* (2013.01)

(58) Field of Classification Search
CPC . G02C 7/02; G02C 7/022; G02C 7/04; G02C 7/049; G02C 11/10; A61F 2/1624;
(Continued)

(56) References Cited

U.S. PATENT DOCUMENTS 6,730,123 B1 * 5/2004 Klopotek .............. A61F 2/1635
623/6.22
2007/0291224 A1 12/2007 Lai
(Continued)

OTHER PUBLICATIONS

International Search Report and Written Opinion dated Dec. 23, 2014 in connection with PCT/US2014/054698.

*Primary Examiner* — Darryl J Collins
(74) *Attorney, Agent, or Firm* — Hammer & Associates, P.C.

(57) ABSTRACT

One aspect of the present disclosure relates to a remotely controllable lens device. The lens device can include a lens material and a circuit physically coupled to the lens material. The circuit can be configured to be powered based on an energy signal from a power source to perform a function (e.g., release of drug, generation of electromagnetic radiation, detection of electromagnetic radiation, and/or control of an optical refractive property). For example, the power source can be an external power source and/or an auto-powered source. The external power source can be, for example, a power source that utilizes synchronized magnetic flux phase coupling (e.g., WiTricity). The auto-powered
(Continued)

source can be provided on-site (e.g., on-chip) using a harvesting system (e.g., solar-cell, photo-cell, piezoelectric, etc.)

25 Claims, 10 Drawing Sheets

(51) Int. Cl.
*G02C 7/04* (2006.01)
*A61F 2/16* (2006.01)

(58) Field of Classification Search
CPC .... A61F 2/1627; A61F 2/1629; A61F 2/1632; A61F 2/1635
USPC ............ 351/159.01, 159.02, 159.03, 159.39, 351/159.4
See application file for complete search history.

(56) References Cited

U.S. PATENT DOCUMENTS

| | | | |
|---|---|---|---|
| 2008/0027304 A1 | 1/2008 | Pardo et al. | |
| 2010/0016704 A1 | 1/2010 | Naber et al. | |
| 2010/0103369 A1* | 4/2010 | Pugh | A61F 9/023 351/158 |
| 2012/0235500 A1 | 9/2012 | Ganem et al. | |
| 2013/0282117 A1* | 10/2013 | Van Heugten | A61F 2/14 623/6.22 |
| 2014/0084489 A1* | 3/2014 | Etzkorn | G02C 7/049 257/778 |
| 2015/0190279 A1* | 7/2015 | Acharya | A61K 9/0051 604/290 |

* cited by examiner

REMOTELY CONTROLLABLE LENS DEVICE

CROSS-REFERENCE TO RELATED APPLICATIONS

This application represents the national stage entry of PCT International Application No. PCT/US2014/054698 filed Sep. 9, 2014, which claims the benefit of U.S. Provisional Application No. 61/875,378, filed Sep. 9, 2013, both of which are hereby incorporated herein by reference for all purposes.

TECHNICAL FIELD

The present disclosure relates generally to a remotely controllable lens device and, more specifically, to systems and methods that employ the remotely controllable lens device to perform one or more functions.

BACKGROUND

This research was supported by the Center for Advanced Soft-Electronics (Global Frontier Project, CASE-2015M3A6A5072945, 30%) of the National Research Foundation (NRF) funded by the Ministry of Science and ICT, Korea. This work was also supported by the World Class 300 Project (S2482887, 70%) funded by the Ministry of SMEs and Startups, Korea.

Generally, an ocular disease affects the eye and/or the visual system. Examples of ocular diseases include diabetic retinopathy, ocular neovascularization, age-related macular degeneration, microbial keratitis, glaucoma, cataract, and presboyopia. Some ocular diseases, like diabetic retinopathy, ocular neovascularization, age-related macular degeneration, microbial keratitis, and glaucoma, can be treated using a contact lens placed directly on the surface of the eye. One type of contact lens that can be used to treat these ocular diseases is a drug eluding contact lens. For example, drug eluding contact lenses can employ polymeric hydrogels that incorporate the drug solution, store the drug within a hollow section, or immobilize the drug on the surface. In each case, the drug eluding contact lens can release drugs into the eye in a sustained manner. However, many ocular diseases can be better treated using a contact lens with a controllable drug delivery system (e.g., based on a sensor recording of a molecule within the eye) rather than the sustained drug delivery provided by the eluding contact lens. While sensors can be embedded in contact lenses (e.g., a glucose oxidase sensor to measure tear glucose level, a pressure sensor to measure intraocular pressure, etc.), they can be complex, bulky, and impractical.

Other ocular diseases, like cataracts and presboyopia, can be treated using an intraocular lens, which can be implanted within the eye during refractive surgery. While such refractive surgery can replace a crystalline lens that is aged or diseased, the intraocular lens generally cannot correct the patient's distance vision and/or the active change of dioptric power. Accordingly a multi-focusing intraocular lens may increase the visual acuity of patients with an intraocular lens.

SUMMARY

The present disclosure relates generally to a remotely controllable lens device and, more specifically, to systems and methods that employ the remotely controllable lens device to perform one or more functions. For example, the one or more functions can include release of a drug, generation of electromagnetic radiation, detection of electromagnetic radiation, and/or control of an optical refractive property (e.g., a focal length of the lens, an optical transmission of the lens, and/or an attenuation of the lens). Other examples of additional functionality can include detection of a molecule, a detection of a mechanical property, a detection of a force, and/or a collimation of electromagnetic radiation.

In one aspect, the present disclosure can include a remotely controllable lens device. The lens device can include a lens material and a circuit physically coupled to the lens material. The circuit can be configured to be powered based on an energy signal from a power source to perform a function (e.g., release of drug molecule, generation of electromagnetic radiation, detection of electromagnetic radiation, and/or control of an optical refractive property). The power source can be, for example, an auto-powered source (e.g., light absorbed by a component of the circuit) and/or an external power source (e.g., a power source that utilizes synchronized magnetic flux phase coupling).

In another aspect, the present disclosure can include a system that can employ a remotely controllable lens to perform a function (e.g., release of drug, generation of electromagnetic radiation, detection of electromagnetic radiation, and/or control of an optical refractive property). The system can include the lens device (e.g., configured as a contact lens or an intraocular lens) and a power source. The lens device can include a lens material and a circuit physically coupled to the lens material. The circuit can be configured to be powered based on an energy signal from a power source to perform a function. The power source can be, for example, an auto-powered source (e.g., light absorbed by a component of the circuit) and/or an external power source (e.g., a power source that utilizes synchronized magnetic flux phase coupling).

In a further aspect, the present disclosure can include a method for employing a remotely controllable lens to perform a function (e.g., release of drug molecule, generation of electromagnetic radiation, detection of electromagnetic radiation, and/or control of an optical refractive property). The method can include steps that steps can include: receiving an energy signal at a circuit physically coupled to a lens device from a power source; powering the circuit based on the energy signal; and performing a function at the circuit. The power source can be, for example, an auto-powered source (e.g., light absorbed by a component of the circuit) and/or an external power source (e.g., a power source that utilizes synchronized magnetic flux phase coupling).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
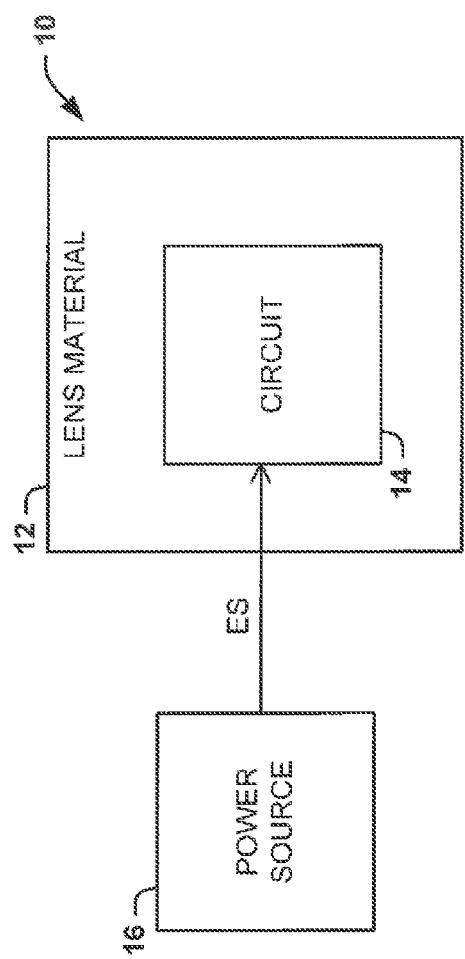
FIG. 1 is a schematic block diagram showing a system that can employ a remotely controllable lens device to perform one or more functions in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "lens device" can refer to an optical device with two opposite surfaces (e.g., both surfaces curved or one curved surface and one planar surface). At least a substantial portion of the lens device can be constructed from a biocompatible lens material that is substantially transparent to visible light. Examples of lens devices can include a contact lens device and an intraocular lens device.

As used herein, the term "remotely controllable lens device" can refer to a lens device in which the lens material is physically coupled a circuit that can facilitate the performance of one or more functions. In some instances, the circuit can be configured to receive a power signal and transmit/receive a communication signal at substantially the same time.

As used herein, the term "circuit" can refer to device that creates a path in which electrons can flow. In some instances, the circuit can be a miniaturized microelectronic system that can be physically coupled to a lens material in a manner that does not substantially impede a patient's vision. As an example, the microelectronic system can provide a modular platform in which one or more integrated circuit modules can be exchanged based on the desired functions of the circuit.

As used herein, the term "function" can refer to an action that can be facilitated and/or performed by the circuit.

As used herein, the term "biocompatible material" can refer to a material that can perform a medical application without eliciting undesirable (e.g., toxic, injurious, etc.) local or systemic effects in the patient.

As used herein, the terms "substantial" and "substantially" can refer to a large amount, which can be complete, but need only be a majority.

As used herein, the term "substantially transparent" can refer to a condition of a lens device in which at least 50% of the lens material is transparent to visible light. In some instances, at least 75% of the lens material is transparent to visible light. In other instances, at least 85% of the lens material is transparent to visible light. In still other instances, at least 90% of the lens material is transparent to visible light. In further instances, at least 95% of the lens material is transparent to visible light.

As used herein, the term "real-time" can refer to a system or method in which input data is processed quickly (e.g., within milliseconds) so that feedback related to the data it is available immediately or almost immediately (e.g., within milliseconds).

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to a remotely controllable lens device and, more specifically, to systems and methods that employ the remotely controllable lens device to perform one or more functions. The remotely controllable lens device can include a circuit physically coupled to a lens material. Advantageously, the circuit can have the ability to facilitate and/or perform the one or more functions, as well as transfer/receive data related to the one or more functions and receive power (e.g., from one or more external power sources and/or auto-powered sources) wirelessly. The data and power can be transferred wirelessly at the same time at least because the different transfers can employ different wireless protocols.

In some instances, the one or more functions can include release of a drug (e.g., releasing a controlled amount on demand), generation of electromagnetic radiation, detection of electromagnetic radiation, and/or control of an optical refractive property (e.g., a focal length of the lens, an optical transmission of the lens, and/or an attenuation of the lens). The remotely controllable lens device can provide additional functionality including, for example, detection of a molecule, a detection of a mechanical property, a detection of a force, and/or a collimation of electromagnetic radiation. The functions can facilitate one or more applications, including diagnosis of a disease or condition (e.g., real time non-invasive biomedical monitoring), treatment of a disease or condition (e.g., smart drug delivery), creation of a human machine interface (e.g., for rehabilitation, entertainment, gaming, augmenting vision for military applications, wearable computing, and/or eye-controlled devices), and the like.

III. Systems

As shown in FIG. 1, one aspect of the present disclosure can include a system 10 that can employ a remotely controllable lens device to perform one or more functions. The remotely controllable lens device can include a lens material 12 and a circuit 14. In some instances, the circuit can also include a mechanism to receive a wireless power signal from an external power source, a mechanism to generate power within the circuit (e.g., to auto-power the circuit), a mechanism to communication with an external computing device, and/or a mechanism to perform to facilitate the one or more functions. In some instances, at least a portion of the remotely controllable lens device can include a protective device, material, and/or coating configured to protect a patient's eye, the circuit 14, and/or the lens material 12 from one or more of the functions.

The circuit 14 can be physically coupled to the lens material 12. For example, the lens material 12 can be configured to transmit or refract optical rays and/or other electromagnetic radiation (e.g., based on one or more curvatures of the lens material). Additionally, the lens material 12 can be constructed from at least one biocompatible material. As an example, the biocompatible material can be substantially transparent to visible light. In some instances, the lens material 12 can be a soft and/or a permeable material, such as a polymeric material (e.g., an elastic polymeric material), a hydrogel, and/or a nanostructured material. In other instances, the lens material 12 can include polymers such as poly(methylmethacrylate) (PMMA) or PHEMA, and/or silicon materials.

In some instances, the functions can be performed to facilitate non-invasive drug delivery (e.g., automatic drug delivery, controlled drug deliver, and/or on demand drug delivery). In other instances, the functions can be performed to facilitate creation of a human-machine interface. Examples of functions that can be performed by the remotely controllable lens device can include release of a drug, generation of electromagnetic radiation, detection of electromagnetic radiation, and/or control of an optical refractive property (e.g., a focal length of the lens, an optical transmission of the lens, and/or an attenuation of the lens). Other examples of additional functionality can include detection of a molecule, a detection of a mechanical property, a detection of a force, and/or a collimation of electromagnetic radiation.

Figure 2:
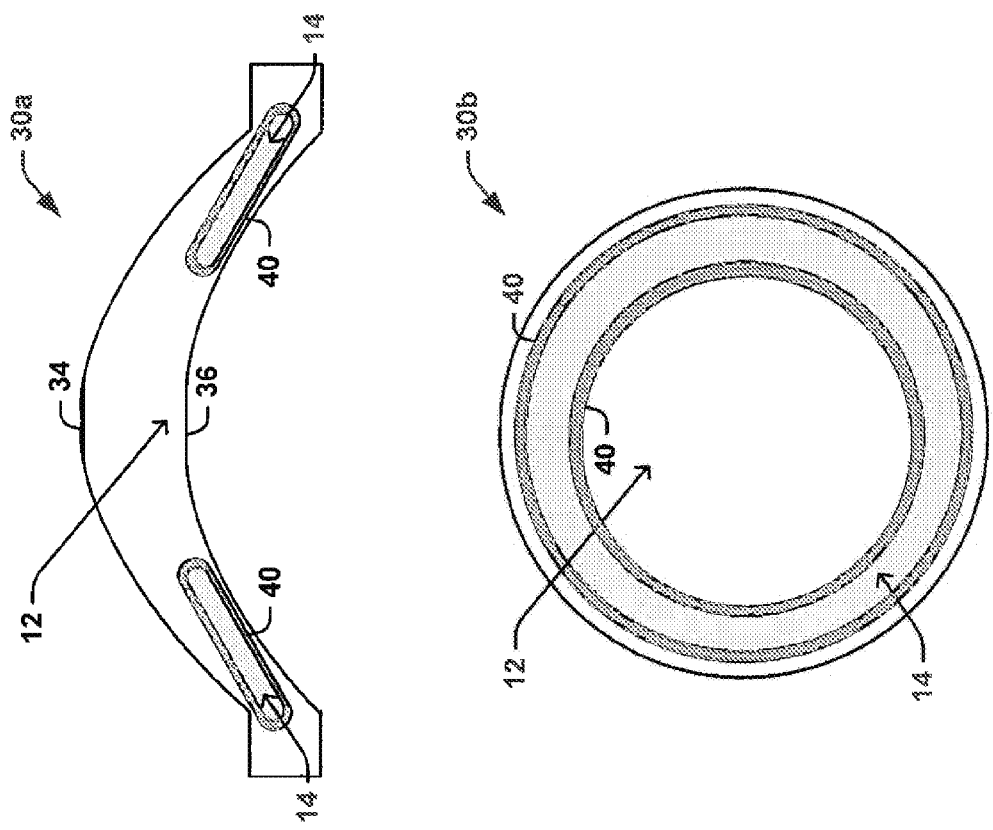
FIG. 2 is a schematic illustration of the remotely controllable lens that can be part of the system shown in FIG. 1.

In some instances, the remotely controllable lens device can be configured to be worn by a patient. In these instances, the remotely controllable lens device can be configured to perform the one or more functions regardless of the patient's position and/or activity level. For example, the remotely controllable lens device can be configured as a contact lens device. An example of a contact lens device is shown in FIG. 2 (30a side view, 30b top view). The contact lens device can include the lens material 12 and the circuit 14. The lens material 12 can have a first surface 34 that has a first curvature and a second surface 36 that has a second curvature. The first curvature and the second curvature facilitate the transmission of optical rays. In this example, the first curvature and the second curvature are both positive so that contact lens device can fit over the cornea. The circuit 14 is located at the periphery of the contact lens device so that a substantial portion of the lens material 12 is substantially transparent to visible light. Optionally, the contact lens device can also include a remotely insulating layer 40.

Figure 3:
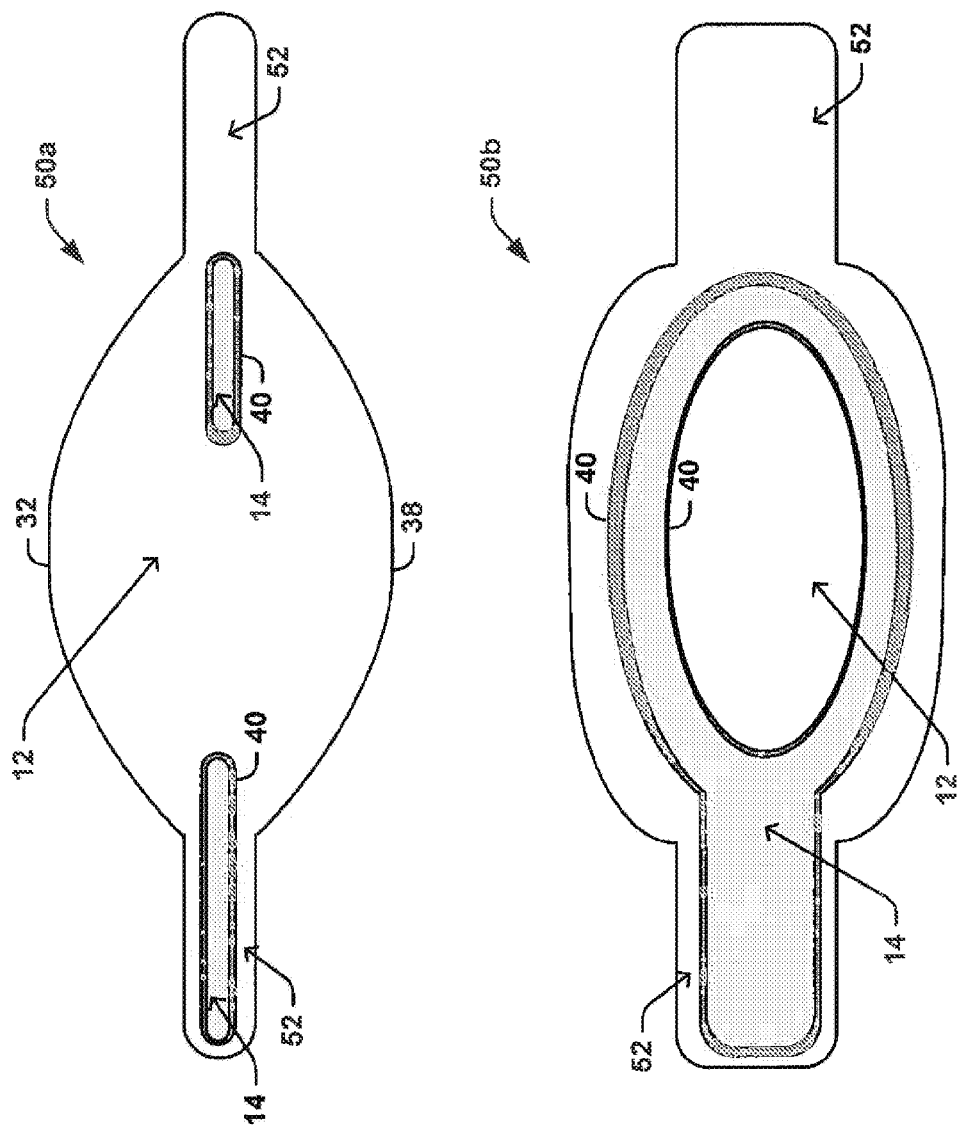
FIG. 3 shows a schematic illustration of a remotely controllable contact lens that can be part of the system shown in FIG. 1.
Figure 4:
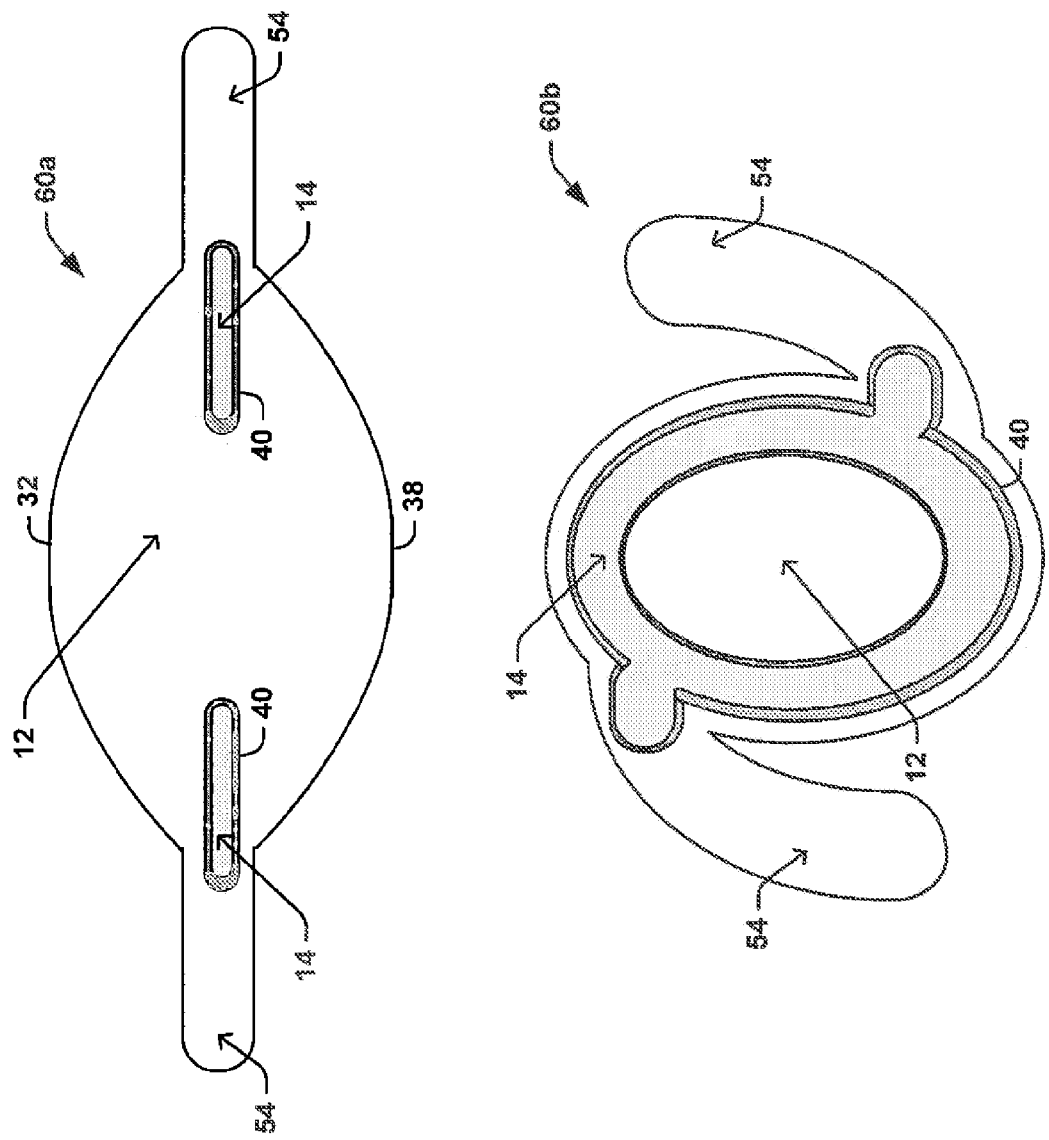
FIGS. 4 and 5 show schematic illustrations of electrically controllable intraocular lenses that can be part of the system shown in FIG. 1.

As another example, the remotely controllable lens device can be configured as an intraocular lens device. Examples of different intraocular lens devices are shown in FIGS. 3 and 4 (40a side view, 40b top view and 50a side view, 50b top view, respectively). In both examples, the intraocular lens device can include the lens material 12 and the circuit 14. The lens material 12 can have a first surface 32 that has a first curvature and a second surface 38 that has a second curvature. The first curvature and the second curvature facilitate the transmission of optical rays. In this example, the first curvature can be positive and the second curvature can be negative, so that contact lens device can fit into the cornea. In both examples, the circuit 14 is located at the periphery of the intraocular lens device so that a substantial portion of the lens material 12 is substantially transparent to visible light. In both examples, the intraocular lens employs side struts (or haptics) 52 fabricated from the same or similar material as the lens material 12. Optionally, the contact lens device and/or hepatics 52 can also include a remotely insulating layer 40.

Referring again to FIG. 1, the circuit 14 can be substantially biocompatible and flexible. In some instances, the circuit 14 can be attached (e.g., soldered and coated with a transparent and/or biocompatible material, like SU8 photoresist, to ensure that the remotely controllable lens device has a smooth surface) to the lens material 12. In other instances, the circuit 14 can be located within the lens material 12.

Due to size and vision constraints (e.g., the patient's pupil must be clear of the circuit 14) and the curvature of the lens material 12, the circuit 14 can be implemented within a small scale when compared to the size of the lens material 12. In some instances, the circuit 14 can be a miniaturized circuit. In some instances, the miniaturized circuit can be implemented within a sub-centimeter sized die area. In other instances, the miniaturized circuit can be implemented within a sub-millimeter sized die area. In still other instances, the miniaturized circuit can be implemented within a total die area of 2 mm$^2$. The miniaturized circuit can have a thickness that does not substantially change the thickness of the lens material 12. In some instances, the thickness can be 1 millimeters or less. In other instances, the thickness can be 0.1 millimeters or less. In still further instances, the thickness can be 0.01 millimeters or less. The miniaturized circuit can have a weight that does not substantially increase the weight of the lens material 12. In some instances, the circuit 14 can have a weight of 5 g or less. In other instances, the circuit 14 can have a weight of 3 g or less. In other instances, the circuit 14 can have a weight of 1 g or less. In addition to the small size, in some instances, the circuit 14 can be highly or totally integrated. An example of a miniaturized integrated circuit can include a CMOS analog integrated circuit that can utilize miniaturized CMOS technology (e.g., the 90 nm CMOS process). In some instances, the small scale of the circuit 14 can allow the circuit to be physically coupled to the lens material 12 in a manner such that the circuit does not substantially impede the patient's vision. In one example, the circuit 14 can be physically coupled to at least a portion of the periphery of the lens material 12. An example illustration (side view 90a and top view 90b) of the remotely controllable lens is shown in FIG. 2 with circuit 14 positioned in the periphery of the lens material 12.

The circuit 14 can be configured to perform and/or facilitate the performance of the one or more functions upon receiving power. In some instances, the circuit can include an auto-power mechanism (e.g., one or more photovoltaic cells). In other instances, the circuit 14 can include a mechanism that allows the circuit to receive a wireless energy signal (ES) from an external power source. In still other instances, the circuit 14 can include both the auto-power mechanism and the mechanism that allows the circuit to receive the wireless energy signal (ES) from the power source 16. For example, the energy signal (ES) can include an electrical signal that transmits electrical power, an electro-magnetic signal that transmits electro-magnetic power, and/or a magnetic signal that transmits magnetic power. In some instances, the power source can be an external power source (e.g., a power source that utilizes synchronized magnetic flux phase coupling) and/or an auto-powered source (e.g., optical energy harvested by a component of the circuit 14, such as a solar-cell, a photo-cell, and/or a piezoelectric device).

In some instances, the auto-powered source can provide a power to circuit 14 from 50 micro-Watts (μW) to 1000 micro-Watts (μW). In other instances, the external power source energy signal (ES) can deliver a wireless power of at least 5000 micro-Watts (μW) to the circuit 14 from the external power source located at distance of at least 1 centimeter away from the circuit. In still other instances, the external power source energy signal (ES) can deliver a wireless power of at least 400 micro-Watts (μW) to the circuit 14 from the external power source located at distance of at least 2 centimeters away from the circuit. For example, at least a portion of the external power source 16 can be mounted to an article configured to be worn by the patient, such as eyeglasses, a device configured to anchor on the patient's head (e.g., headband, a hat, a hair clip, etc.), a device configured to anchor on or within the ear, and/or a device configured to be anchored by or housed within a piece of clothing or jewelry.

In some instances, the power source 16 can include an auto-power source that can create power from an optical signal (e.g., visible, infrared, or ultraviolet light, from a solar power source, a light emitting diode, a laser, etc.) and/or an external power source (e.g., that utilizes synchronized magnetic flux phase coupling). One example of a power source that utilizes synchronized magnetic flux phase coupling is a WiTricity power source. For example, the WiTricity power source can utilize a resonance frequency from 100 kHz to 10 MHz. The external power source 16 can also include, for example, a radio frequency power source (frequency from 2.4 GHz to 5 GHz) and/or an electrical power source.

The energy signal (ES) can be sent wirelessly from the power source 16 to the circuit 14 according to one or more wireless protocols. Accordingly, the circuit 14 can include one or more antennas configured to receive the different signals according to the different protocols that can be included within the energy signal (ES). In the example shown in FIG. 5, the circuit 14 has three antennas 92, 94, and 96 for power transfer and communication each wrapped around the periphery of the lens material 12. For example, antenna 92 can be a WiTricity antenna for power transfer, antenna 94 can be a photocell antenna (e.g., or photovoltaic cell array) that can gather power for auto-powering the circuit 14, and antenna 96 can be a radio frequency data antenna for communication. This configuration allows portions of the energy signal (ES) can include a power signal from a photocell and a WiTricity power signal. Data can be transferred to and from the circuit within a radio frequency data communication signal (or via a different type of communication signal, such as an optical data communication signal).

In some instances, the photocell antenna can be an energy-autonomous, photovoltaic (PV)-driven and MRI compatible CMOS implantable sensor. On-chip p+/n-well diode arrays are used as CMOS-compatible PV cells to harvest μW's of power from the light that penetrates into the tissue. As an example, these PV cells can be fabricated using CMOS 90 nm technology. When operating in sunlight or a bright artificial light environment, optical energy can activate the PV cell array and generate a voltage at the output. The solar PV cells can be capable of generating a floating source voltage and current sufficient to drive and power the circuit (especially in natural sunlight). The PV cells can exhibit a 4V output, provides true wireless power, and dies not exhibit EMI/RFI generation. In addition the PV cells can exhibit a solid state reliability with an 140 mΩ internal synchronous rectifier, a 120 mΩ internal power active switch, and a controlled duty cycle (e.g., by a maximum power point tracking (MPPT) algorithm).

Figure 5:
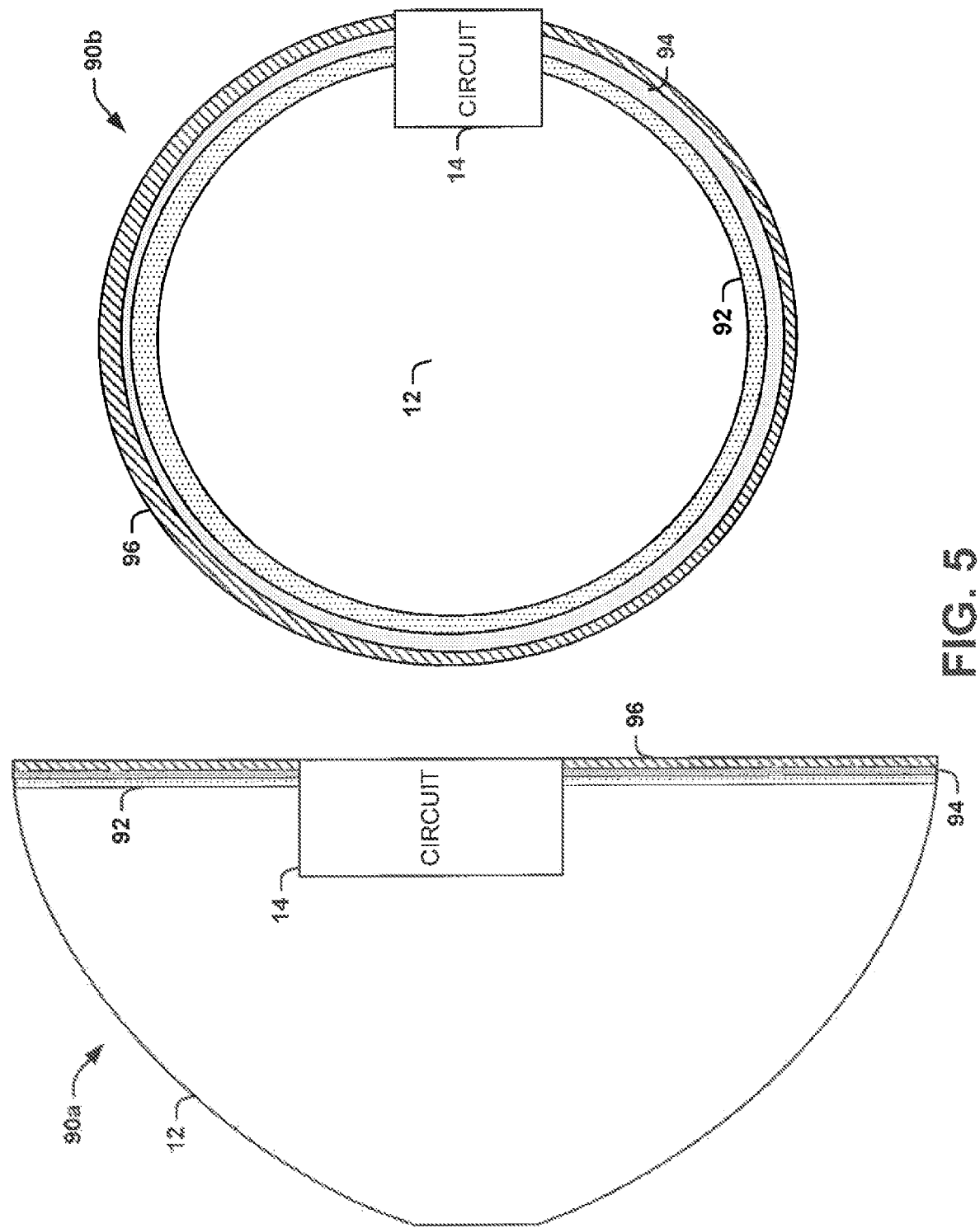
Figure 6:
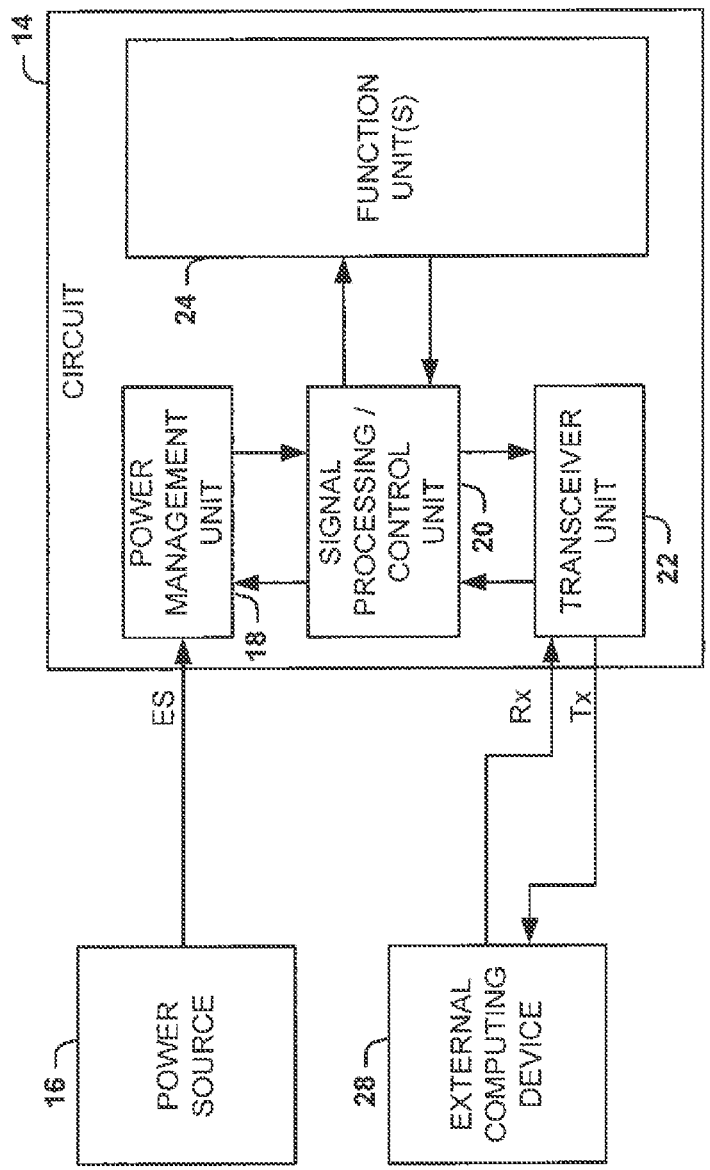
FIG. 6 is a schematic block diagram showing a circuit that can be part of the system shown in FIG. 1.

As illustrated in FIG. 6, by employing different antennas (e.g., as shown in FIG. 5) and/or different modular units, the circuit 14 can both receive the wireless energy signal (ES) from the power source 16 and transfer/receive data (Tx/Rx) with an external computing device 28 (e.g., to facilitate remote control of the one or more functions and/or to create a human/machine interface based on the one or more functions) at substantially the same time. The circuit 14 can include a power management unit 18, a signal processing/control unit 20, a transceiver unit 22, and one or more function units 24.

The power management unit 18 can be configured to receive the energy signal (ES) from the power source 16 and ensure reliable functionality of the circuit 14. In some instances, the power management unit 18 can determine when the power received goes below a predefined value (e.g., a value of power that is at least enough to perform or facilitate the one or more functions) and starts an emergency procedure to facilitate shutting down the remotely controllable lens device. To prevent such a shut down, in some examples, the power source 16 can include a plurality of sources that contribute to the energy signal (ES). This ensures the power efficiency and robustness of the system against any failure or drop of power output in any one of the sources. In some instances, the power management unit 18 can store a portion of power transmitted via the energy signal (ES) for conditions where the energy signal (ES) is below the predefined value.

The transceiver unit 22 can be configured to transmit (Tx) data to and receive (Rx) data from an external computing device 28 (e.g., via wireless communication such as radio frequency communication, electromagnetic communication, or the like). In some instances, the data exchanged with the external computing device 28 can facilitate remote control of the one or more functions and/or to create a human/machine interface based on the one or more functions.

In some instances, the data exchanged between the transceiver unit 22 and the external computing device 28 can be based on the function and/or related to the function. For example, the external computing device 28 can communicate with the transceiver unit 22 of the remotely controllable lens device for real time data visualization, processing, storage, additional communication, and/or generation of alarms and/or warnings. For example, the external computing device 28 can include a cellular phone, a smartphone, a tablet computing device, a laptop computing device, a desktop computing device, or the like. In some instances, the external computing device 28 can distribute the monitoring and control functionalities over wireless networks (e.g., WiFi, GSM, 3G, etc.) allowing for real time remote access and/or teleoperation.

Figure 7:
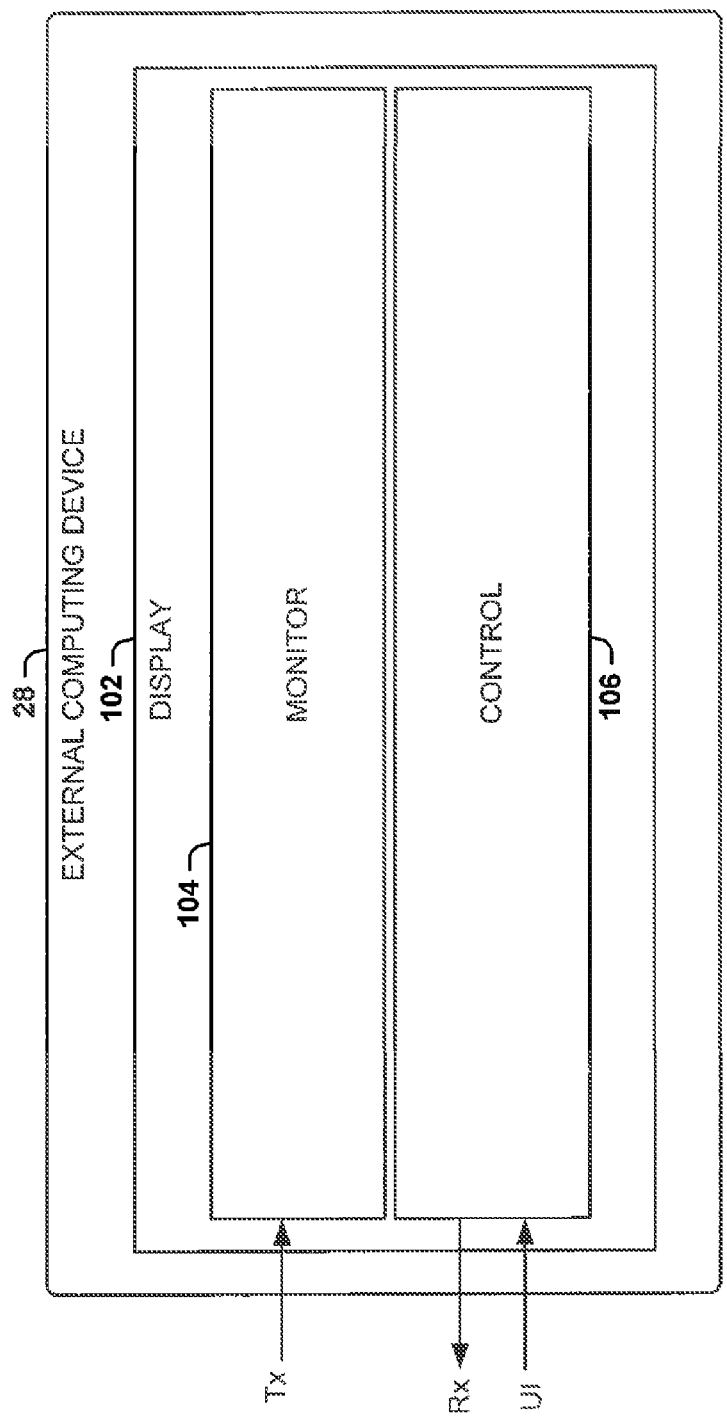
FIG. 7 is a schematic block diagram showing an external computing device with a graphical user interface that can be part of the system shown in FIG. 6.
Figure 8:
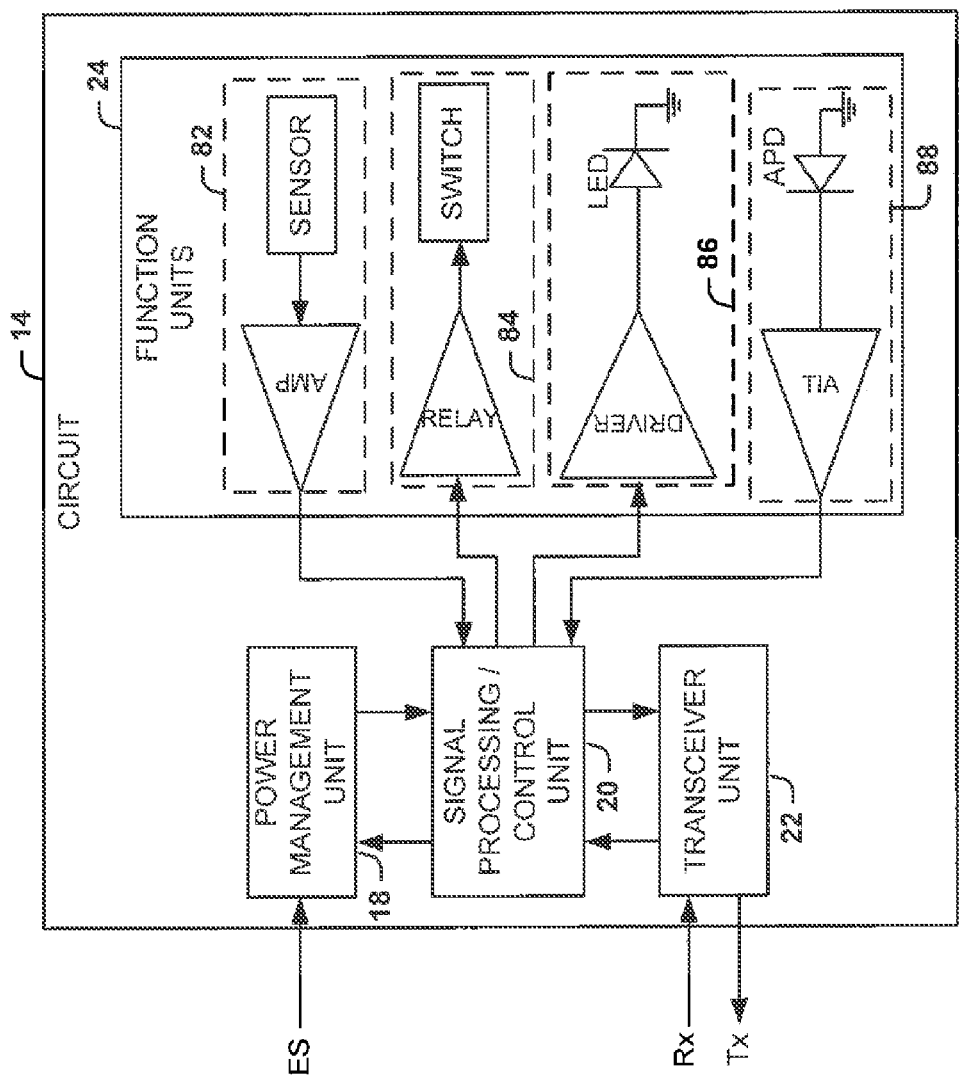
FIG. 8 is a schematic block diagram showing example function units that can be part of the circuit shown in FIG. 6.

As shown in FIG. 7, an example, the external computing device 28 can include a display 102, an input/output mechanism, and/or a graphical user interface. According to the example of FIG. 7, the display 102 can show a monitoring visualization 104 and a control visualization 106. The monitoring visualization 104 can display one or more monitoring parameters (e.g., a numerical value, a graphical progression of historical values, etc.) based on data received (Tx) from the remotely controllable lens device. The control visualization 106 transmit a control signal (Rx) to the remotely controllable lens based on the data received (Tx). In some instances, the control signal (Rx) can be further based on a user input (UI) to the external computing device 28. As an example, the circuit can transmit data related to a sensed molecule within the patient's eye (e.g., a glucose concentration within one or more tears) to the external computing device 28. The monitoring visualization 104 can display the glucose concentration, and the control visualization 106 can transmit a control signal to the circuit 14 instructing the circuit 14 to facilitate the release of a specific amount of a drug over a specific time period (e.g., via controlling a microswitch). In some instances, the control visualization 106 can receive a user input (UI) that can set at least a part of the control signal.

Referring again to FIG. 6, the signal processing/control unit 20 can be configured to communicate (e.g., in a bidirectional fashion) with the power management unit 18, the transceiver unit 22, and the one or more function units 24. In some instances, the signal processing/control unit 20 can control one or more of the modular units based on the communication. In other instances, the signal processing/control unit 20 can process one or more signals (e.g. according to adaptive noise removal and/or filtering mechanisms) received from one or more of the modular units. For example, the signal processing can make the circuit 14 robust against environment disturbances, such as patient motion. For example, the signal processing/control unit 20 can receive real-time information from the power management unit 18, the transceiver unit 22, and/or the function unit(s) 24 and provide control information to one or more of these units in real time. In some instances, one or more of the function units 24 can be implemented on the lens material 12 using flip chip technology, which utilizes low temperature solder and micropositioner.

The function unit(s) 24 can be configured to perform or facilitate the function of the remotely controllable lens. An example of a plurality of function units 24 is shown in FIG. 5. As illustrated, the function units 24 can include an optical refractive property control function unit 82, a drug release function unit 84, an electromagnetic radiation generation unit 86, and an electromagnetic radiation detection unit 88. Although these function units 24 can be implemented together on the same electrically controllable lens, these function units 24 need not be implemented together. Additionally, other function units can be included within the function units 24, such as a molecular detection functional unit, a mechanical property detection functional unit, a force detection functional unit, an electromechanic radiation collimation functional unit, or the like.

The function units 24 can exchange data with the signal processing/control unit 20. For example, the optical refractive property control function unit 82 and the electromagnetic radiation detection unit 88 can transmit data to the signal processing/control unit 20, while the drug release function unit 84 and the electromagnetic radiation generation unit 84 can receive data from the signal processing/control unit.

In some instances, the function units can be configured to control an optical refractive property of the lens device. The sensor in block 82 can detect a change in the environment that would require a change in the optical refractive property (e.g., pressure, light, etc.). The sensor can transmit a signal to the signal processing/control unit, and the signal processing/control unit can cause a component to change the optical refractive property. For example, the remotely controllable lens device can include a transmission filter (that includes one or more optical materials that can have a polarization dependent transmission so as to attenuate one state of polarization more than another state of polarization to enhance visual charity in bright day light, such as thin layers of nematic crystals) that can be capable of varying the transmission efficiency of light. The transmission filter can be controlled electrically on demand. For example, the sensor can be a light (e.g., UV, visible, infrared, etc.) detector that can measure a property of the light and the signal processing/control unit 20 can generate a signal to control a transmission characteristic of the transmission filter. As an example, the transmission filter can function similarly to sun glasses with an automatically adjustable transmission characteristic and/or optical density.

As another example, the optical refractive property can be focus tuning. For example, the intraocular lens device can be configured to be inserted into a patient's lens capsule of an eye after removal of the cortex and the nucleus of the crystalline lens. The lens capsule can be elastically deformable in response to the tension of zonular fibers connecting the lens capsule to the cilliary body. A sensor within the circuit 14 can detect the tension in the zonular fibers and facilitate tuning the focus of the intraocular lens device. For example, the sensor can utilize an electromechanical sensing mechanism to generate an electrical signal in relation to the shape of the deformation of the lens capsule. The electrical signal can be transmitted to the circuit 14 to control the refractive properties.

For example, the circuit 14 can include at least one piezoelectric material. In response to an applied voltage to the piezoelectric material, the circuit 14 can mechanically change the first curvature and/or the second curvature (e.g., from the original state to a flattened state). For an incoming collimated optical beam, this mechanical change can result in a shift of the focus from an original point to a new point. This tuning function can be useful to assist accommodation, particularly for a person with presbyopia. There are several alternative mechanisms available for tuning actuation, such as a fluidic valve, thermal control of temperature sensitive polymer, etc.

In other instances, the function units 24 can be configured for controlled drug release. A signal can be transferred to block 84 from the signal processing/control unit 20 through a relay to open the switch. Upon opening the switch, the drug can be released from the circuit 14 and through a release region in the remotely controllable lens device. For example, the drug can be delivered into a tear film and eventually to a target tissue of the person (e.g., blood circulation, the vitreous, the retina, the cornea, etc.).

The function units 24 can facilitate short-term drug delivery and/or long-term drug delivery. In an example of short-term drug delivery, one or more drug-coated gold nanoparticles can be attached to a gold antenna by thiol linkages. The drug molecules can be coated on gold nanoparticles by physical binding such as hydrophobic interaction and chemical binding by covalent bonding via Au-thiol chemistry. The attached gold nanoparticles and drug molecules can be detached from gold antenna in a sustained manner over a specific period of time or they can be triggered for release by stimulation including electrical signal, thermal stimulation, light irradiation, and so on. In an example of long-term drug delivery, the drug can be stored in drug reservoirs coated with an Au membrane. The Au membrane is designed to be dissolved in the form of $AuCl_4^-$ in NaCl solution by electrical current. Each reservoir is sealed at one end with a thin membrane of gold anode which dissolves in the body fluid in response to an electric potential. After dissolution of the Au membrane to $AuCl_4^-$ in body fluid, the drug in the opened reservoir can be diffused out of the reservoir and delivered through the eye to the body. Examples of drug molecules that can be used for short-term delivery and/or long-term delivery can include diabetic drugs (e.g., insulin, dipeptidyl peptidase-4 inhibitors, and/or GLP-1 peptide and its analogues) and anti-angiogenic drugs for the treatment of ocular neovascularization (e.g., peptide drugs, such as anti-Flt1 peptide, anti-VEGF antibodies, and/or chemical drugs).

As an example, the controlled drug release can be controlled based on a sensor that receives at least one type of molecule present in tears and/or the eye (e.g., the vitreous) and transmits the signal to the control unit. The control unit can generate the signal that opens the switch based on the sensor signal. Examples of the sensor can include a glucose oxidase sensor that can monitor the tear glucose level and/or a VEGF sensor that can assess ocular angiogenesis. In some instances, the sensor and the drug delivery function unit can be integrated within block 84.

In still other instances, the function units 24 can be configured for optical transmission. For example, the LED of block 86 can be configured to transmit a light signal (e.g., ultraviolet, visible, infrared, etc.) from the circuit 14 to provide optical communication. As an example, the LED can be a μ-LED (e.g., using a PMOS transistor with the body terminal tied to the source in order to eliminate the body effect). For example, the μ-LED can provide a novel human-machine interface system. In some instances, the μ-LED can emits red light (e.g., 650 nm) with 100-1000 $mW/mm^2$ intensity. The light emitted can be a quasi-collimated beam of ±30° angle. The LED elements can be of a circular shape and fabricated on a compound semiconductor multilayer structure grown via metal organic chemical vapor deposition with a turn-on voltage of 3V with 400 μW power consumption. Since humans cannot perceive fluctuations in light sources above approximately 60 Hz, duty cycling (e.g., 3% duty cycling at a 1 MHz frequency) can be used to make the LED appear continuously activated to reduce the required power.

In still further instances, the function units 24 can be configured for optical sensing (e.g., by a light sensor, such as a photodetector). For example, the APD of block 88 can be configured as an avalanche photodiode that can generate current by visible light coming into the eye. In some instances, the APD can transmit the current to the signal processing/control unit, which can send the current to the LED of block 86 to drive the LED to emit light. In other instances, a control photovoltaic cell can be utilized as a reference to implement a closed-loop ambient light monitoring and control system.

IV. Methods

Figure 9:
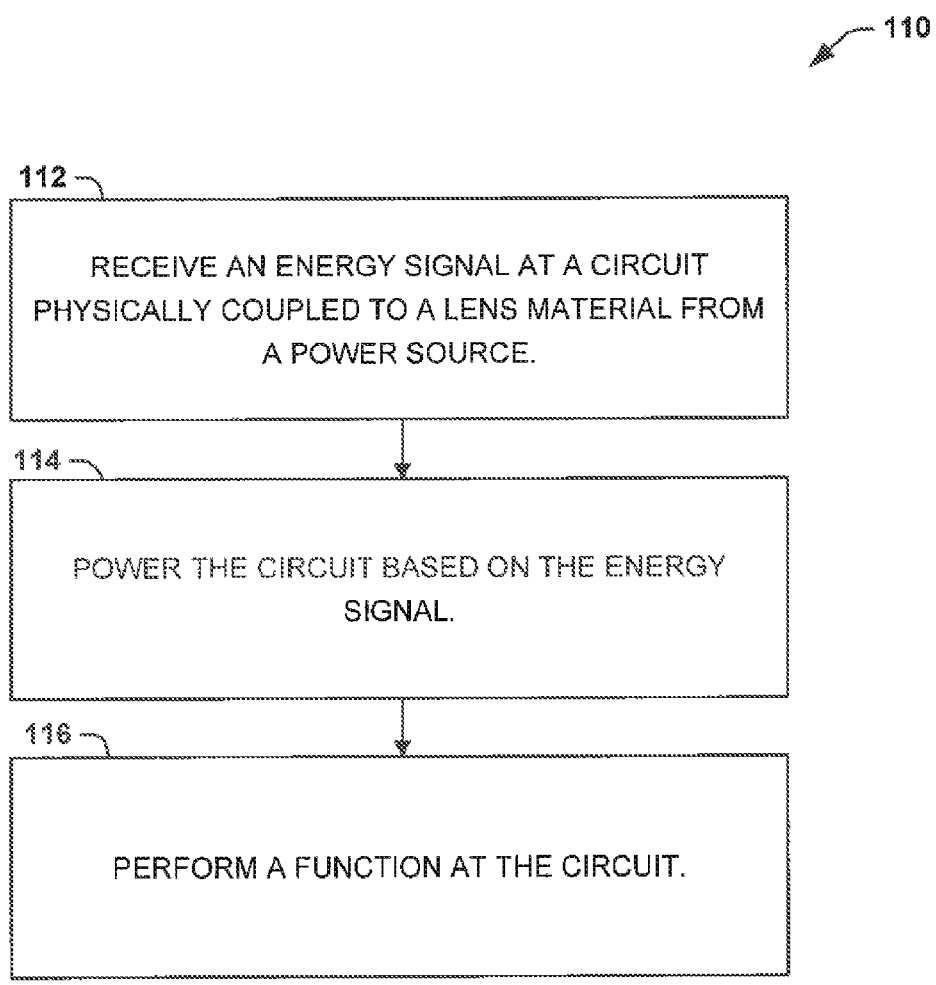
FIG. 9 is a process flow diagram showing a method for performing one or more functions by a remotely controllable lens device in accordance with another aspect of the present disclosure.

Another aspect of the present disclosure can include methods that can employ a remotely controllable lens device to perform one or more functions. An example of a method 110 that can enable a remotely controllable lens device to perform a plurality of functions is shown in FIG. 9. Another example of a method 120 that can facilitate communication between a circuit associated with a remotely controllable lens device and an external computing device is shown in FIG. 10.

Figure 10:
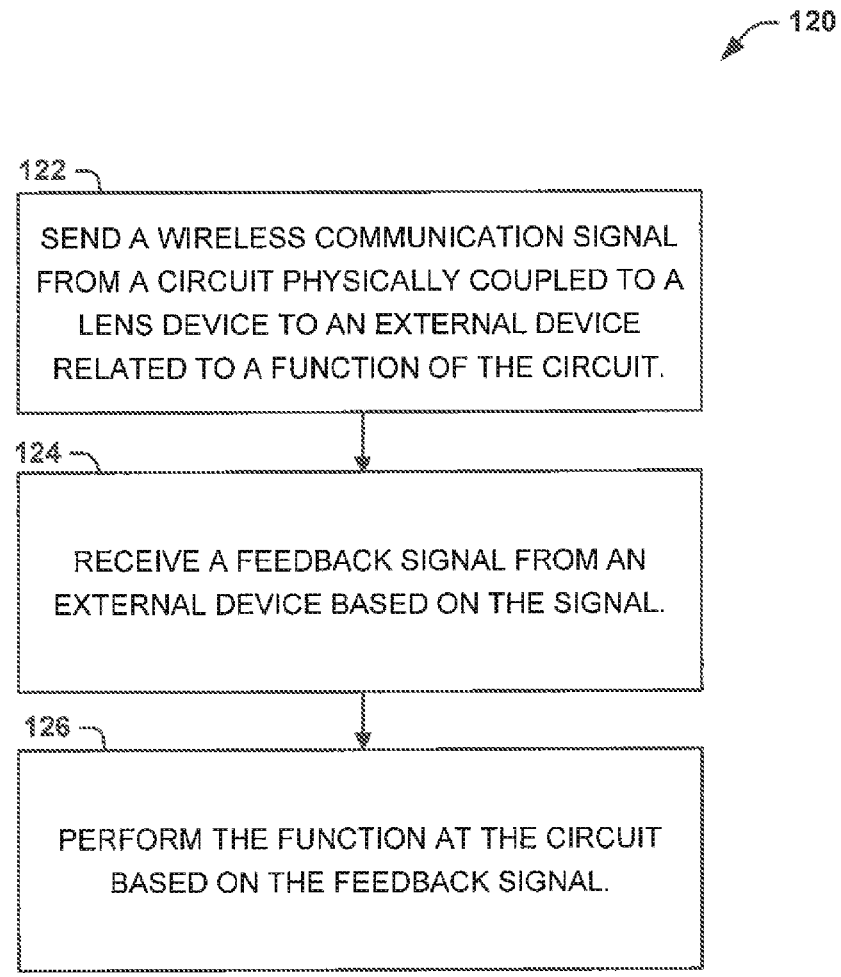
FIG. 10 is a process flow diagram showing a method for communicating between a circuit associated with a remotely controllable lens device and an external computing device in accordance with a further aspect of the present disclosure.

The methods 110 and 120 of FIGS. 9 and 10, respectively, are illustrated as process flow diagrams with flowchart illustrations. For purposes of simplicity, the methods 110 and 120 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 110 and 120.

Referring to FIG. 9, an aspect of the present disclosure can include a method 110 for performing one or more functions by a remotely controllable lens device according to a further aspect of the present disclosure. The remotely controllable lens device can include a lens material and a circuit physically coupled to the lens material and can be configured as a contact lens device or an intraocular lens device.

At 112, an energy signal (e.g., ES) can be received at the circuit (e.g., circuit 14) that is physically coupled to the lens material (e.g., lens material 12). The energy signal can be wirelessly transmitted from a power source (e.g., power source 16). The power source can be, for example, an auto-powered source (e.g., light absorbed by a component of the circuit) and/or an external power source (e.g., a power source that utilizes synchronized magnetic flux phase coupling). In some instances, the auto-powered source can provide a power to circuit 14 from 50 micro-Watts (μW) to 1000 micro-Watts (μW). In other instances, the external power source energy signal (ES) can deliver a wireless power of at least 5000 micro-Watts (μW) to the circuit 14 from the external power source located at distance of at least 1 centimeter away from the circuit. In still other instances, the external power source energy signal (ES) can deliver a wireless power of at least 400 micro-Watts (μW) to the circuit 14 from the external power source located at distance of at least 2 centimeters away from the circuit. In other instances, the external power source can also include, for example, a radio frequency power source and/or an electrical power source.

In some instances, the energy signal can be transmitted from a plurality of different power sources. The transmission can be accomplished according to a plurality of wireless protocols. For example, the energy signal can include an electrical signal that transmits electrical power, an electromagnetic signal that transmits electro-magnetic power, and/or a magnetic signal that transmits magnetic power.

At 114, the circuit can be powered based on the energy signal. At 116, the function can be performed at the circuit upon powering the circuit by the energy signal. In some instances, the functions can be performed to facilitate non-invasive drug delivery (e.g., automatic drug delivery, controlled drug deliver, and/or on demand drug delivery). In other instances, the functions can be performed to facilitate creation of a human-machine interface. Examples of functions that can be performed by the remotely controllable lens device can include release of a drug, generation of electromagnetic radiation, detection of electromagnetic radiation, and/or control of an optical refractive property (e.g., a focal length of the lens, an optical transmission of the lens, and/or an attenuation of the lens). Other examples of additional functionality can include detection of a molecule, a detection of a mechanical property, a detection of a force, and/or a collimation of electromagnetic radiation.

Referring now to FIG. 10, another aspect of the present disclosure can include a method 120 for communicating between a circuit associated with a remotely controllable lens device and an external computing device, according to another aspect of the present disclosure. Like the power transmission, the communication between the circuit and the external computing device also can be wireless. Advantageously, the power transmission and the wireless communication can occur simultaneously. For example, the power transmission and the wireless communication As 122, a wireless communication signal (e.g., Tx) related to a function of the circuit can be sent from the circuit to an external device (e.g., external computing device 28). For example, the signal can be sent by radio frequency (RF) communication and/or optical communication. In response, the external device can send a feedback signal (e.g., Rx) back to the circuit. In some instances, the feedback signal can be a control signal related to the function. For example, the feedback signal can be configured based on one or more user inputs (UI). At 126, the function can be performed at the circuit based on the feedback signal.

From the above description, those skilled in the art will perceive improvements, changes and modifications. Such improvements, changes and modifications are within the skill of one in the art and are intended to be covered by the appended claims.

What is claimed is:

1. A lens device for drug delivery comprising: a lens material; and a circuit physically coupled to the lens material and configured to be powered based on an energy signal from a power source to perform a function, wherein the power source comprises an auto-power source and an external power source that utilizes synchronized magnetic flux phase coupling, the external power source is a WiTricity power source, the circuit includes an antenna for wireless power transfer for gathering power for auto-powering the circuit and an antenna for communication, and the lens device includes a drug delivery system consisting of drug-coated gold nanoparticles attached to one of said antenna and/or drug reservoirs coated with an Au membrane.

2. The lens device of claim 1, wherein at least one of the auto-power source delivers power from about 50 micro-Watts (.mu.W) to 1000 micro-Watts (.mu.W) and the external power source that utilizes synchronized magnetic flux phase coupling delivers power greater than 5000 micro-Watts (.mu.W) at a distance of at least 1 centimeter (cm) and greater than 400 micro-Watts (.mu.W) at a distance of at least 2 centimeters (cm).

3. The lens device of claim 1, wherein the auto-power source comprises a power harvesting system located on the circuit comprising at least one of a solar-cell, a photo-cell, and a piezoelectric device.

4. The lens device of claim 1, wherein the external power source that utilizes synchronized magnetic flux phase coupling utilizes a resonance frequency from 100 kHz to 10 MHz.

5. The lens device of claim 1, wherein the function comprises at least one of a release of a drug from the lens device, a generation of a first electromagnetic radiation from the lens device, a detection of a second electromagnetic radiation at the lens device, and a control of an optical refractive property of the lens device.

6. The lens device of claim 5, wherein the optical refractive property comprises at least one of the focal length of the lens, an optical transmission, and an attenuation.

7. The lens device of claim 5, wherein the function further comprises at least one of a detection of a molecule, a detection of a mechanical property, a detection of a force, and a collimation of electromagnetic radiation.

8. The lens device of claim 1, wherein the lens device is configured as an intraocular lens device or a contact lens device.

9. The lens device of claim 1, wherein the circuit is configured to at least one of transmit a signal via a wireless link to a computing device based on the function and receive a signal from a computing device via the wireless link related to the function.

10. The lens device of claim 1, wherein the power source further comprises at least one of a radio frequency power source in a frequency from 2.4 giga-Hertz (GHz) to 5 giga-Hertz (GHz) and an electrical power source.

11. The lens device of claim 1, wherein the lens material comprises a soft polymeric material.

12. The lens device of claim 11, wherein the soft polymeric material is porous.

13. The lens device of claim 12, wherein the function comprises a controlled release of a drug from the lens device or an on-demand release of the drug from the lens device based on a detection of at least one molecule.

14. A system for drug delivery comprising: a lens device configured as a contact lens device or an intraocular lens device, comprising: a lens material; and a circuit physically coupled to the lens material and configured to perform a function; and a power source configured to transmit an energy signal that powers the circuit, wherein the power source comprises an auto-power source and a power source that utilizes synchronized magnetic flux phase coupling, the external power source is a WiTricity power source, the circuit includes an antenna for wireless power transfer for gathering power for auto-powering the circuit and an antenna for communication, and the lens device includes a drug delivery system consisting of drug-coated gold nanoparticles attached to one of said antenna and/or drug reservoirs coated with an Au membrane.

15. The system of claim 14, wherein the energy signal comprises at least one of an electrical signal, an electromagnetic signal, and a magnetic signal.

16. The system of claim 14, wherein the power source further comprises at least one of a radio frequency power source and an electrical power source.

17. The system of claim 14, wherein the function comprises at least one of a release of drug from the lens device, a generation of a first electromagnetic radiation from the lens device, a detection of a second electromagnetic radiation at the lens device, and a control of an optical refractive property of the lens device.

18. The system of claim 17, wherein the function further comprises at least one of a detection of a second molecule, a detection of a mechanical property, and a collimation of electromagnetic radiation.

19. The system of claim 14, wherein the circuit is configured to communicate wirelessly with a computing device.

20. A method for drug delivery comprising the steps of: receiving an energy signal at a circuit physically coupled to a lens device from a power source; and powering the circuit based on the energy signal; and performing a function at the circuit, wherein the power source comprises of an auto-powered source and a power source that utilizes synchronized magnetic flux phase coupling, the external power source is a WiTricity power source, the circuit includes an antenna for wireless power transfer for gathering power for auto-powering the circuit and an antenna for communication, and the lens device includes a drug delivery system consisting of drug-coated gold nanoparticles attached to one of said antenna and/or drug reservoirs coated with an Au membrane.

21. The method of claim 20, wherein the function comprises releasing a drug from the lens device.

22. The method of claim 20, wherein the function comprises generating electromagnetic radiation from the lens device.

23. The method of claim 20, wherein the function comprises detecting electromagnetic radiation at the lens device.

24. The method of claim 20, wherein the function comprises controlling an optical refractive property of the lens device.

25. The lens device of claim 24, wherein the optical refractive property comprises at least one of the focal length of the lens device, an optical transmission of the lens device, and an attenuation of the lens device.

* * * * *